United States Patent [19]

Karnis et al.

[11] 4,276,119
[45] Jun. 30, 1981

[54] METHOD AND APPARATUS FOR ON-LINE MONITORING OF SPECIFIC SURFACE OF MECHANICAL PULPS

[75] Inventors: Alkibiadis Karnis, Dollard des Ormeaux; Paul M. Shallhorn, Vaudreuil, both of Canada

[73] Assignee: Domtar Inc., Montreal, Canada

[21] Appl. No.: 38,631

[22] Filed: May 14, 1979

[51] Int. Cl.³ .................. D21F 7/06; G01N 21/00
[52] U.S. Cl. .................. 162/49; 73/61 R; 73/61.4; 162/55; 162/263; 209/211; 356/339; 356/342
[58] Field of Search ............... 73/61 R, 61.4; 162/49, 162/198, 263, 55, DIG. 10; 209/237, 211; 356/339, 73, 442

[56] References Cited

U.S. PATENT DOCUMENTS

| | | | |
|---|---|---|---|
| 2,858,727 | 11/1958 | Stamm et al. | 356/339 |
| 3,786,261 | 1/1974 | Tucker | 356/442 |
| 3,802,964 | 4/1974 | Forgacs et al. | 162/263 |
| 3,879,129 | 4/1975 | Inoue | 356/442 |
| 4,135,389 | 1/1979 | Karnis et al. | 209/211 |

FOREIGN PATENT DOCUMENTS 2828843 7/1977 Fed. Rep. of Germany ......... 162/49

OTHER PUBLICATIONS

Johnson et al., "Determination of Dangerous Shives," Paper Given at International Mechanical Pulping Conf. 1973, Jun. 1973.

*Primary Examiner*—S. Leon Bashore
*Assistant Examiner*—Steve Alvo

[57] ABSTRACT

The specific surface distribution of a pulp may be obtained by fractionating the pulp in a hydrocyclone means into an overflow and an underflow fraction and measuring the specific surface of each of the fractions and the amount of each of the fractions and based on a cumulative normal distribution relationship of cumulative weight fraction as a percent of feed to specific surface, determining the specific surface distribution for said pulp.

Also disclosed is a method and apparatus for determining the specific surface of a pulp sample by measuring the light scattering characteristics to obtain a turbidity measurement of the pulp sample, measuring the consistency of the sample and determining the specific surface of said pulp based on the relationship of specific surface to the turbidity measurement for the measured consistency of the pulp.

7 Claims, 4 Drawing Figures

METHOD AND APPARATUS FOR ON-LINE MONITORING OF SPECIFIC SURFACE OF MECHANICAL PULPS

FIELD OF INVENTION

The present invention relates to a method and apparatus for on-line monitoring of specific surface of a mechanical pulp. More specifically, the present invention relates to a method and apparatus for determining the cumulative distribution by weight of specific surface of a pulp.

By the term "mechanical pulps" is understood pulps produced primarily by mechanical processing with or without auxillary steps of chemical or physical nature. Such pulps include conventional (stone) ground wood and refiner groundwood and pulps produced by an array of chemi-mechanical or thermo-mechanical processes.

It has been shown in the art that the fibre properties for mechanical pulp that determine the strength, optical and printing characteristics include amongst other things (a) the average specific surface of the fibres which is important in determining the strength properties of mechanical pump (i.e. tear, tensile, burst, wet web, etc) and some printing properties such as strikethrough, ink absorptivity and which also influences significantly the opacity and brightness of the paper and (b) specific surface distribution of the fibres which affects printing characteristics such as linting.

It has been proposed to determine specific surface of a pulp, on-line using at least two measuring techniques which measure other characteristics of the pulp but wherein each measurement is influenced by specific surface and by solving simultaneous equations to obtain indication of the specific surface of the pulp. This procedure was further complicated by the fact that the technique for measuring consistency also was not a true measurement and further reflected the characteristics of specific surface so the three simultaneous equations had to be solved in order to determine the specific surface (average specific surface) of the pulp. Such a technique is described in the U.S. Pat. No. 3,802,964 issued in 1973 to Forgacs and Karnis.

Most measurements of specific surface utilize the permeability method, however such methods are not well suited for on-line measurements.

BRIEF DESCRIPTION OF THE INVENTION

It is an object of the present invention to provide a method and apparatus for on-line determining the average specific surface and/or the specific surface distribution of a pulp It is yet another object of the present invention to provide an optical system for on-line determining the specific surface of a pulp.

Broadly the present invention also relates to a method and apparatus for determining the fibre specific surface distribution by weight of a pulp comprising: hydrocyclone means for separating pulp fed thereto into an overflow fraction and underflow fraction, means for measuring the specific surface and means for measuring the amount of fibre flow of pulp of at least a selected two of said pulp feed and each of said fractions, determining the specific surface distribution of said pulp fed to said hydrocyclone means based on said measured flows of pulp and specific surfaces of said selected two of said feed, said underflow and said overflow fractions and a cumulative normal distribution relationship of cumulative weight fraction as a percent of feed to specific surface.

The present invention also broadly relates to a process for on-line determination of the specific surface of a pulp suspension which comprises measuring the light scattering characteristics of the pulp suspension and thereby obtaining a measurement of the turbidity of said suspension, measuring the consistency of said suspension and determining the average specific surface of said pulp suspension based on the relationship of specific surface to the turbidity reading for the measured consistency.

BRIEF DESCRIPTION OF THE DRAWINGS

Further features, objects and advantages will be evident from the following detailed description of the preferred embodiments of the present invention taken in conjunction with the accompanying drawings and which.

DETAILED DESCRIPTION OF THE PREFERRED EMBODIMENTS

Figure 1:
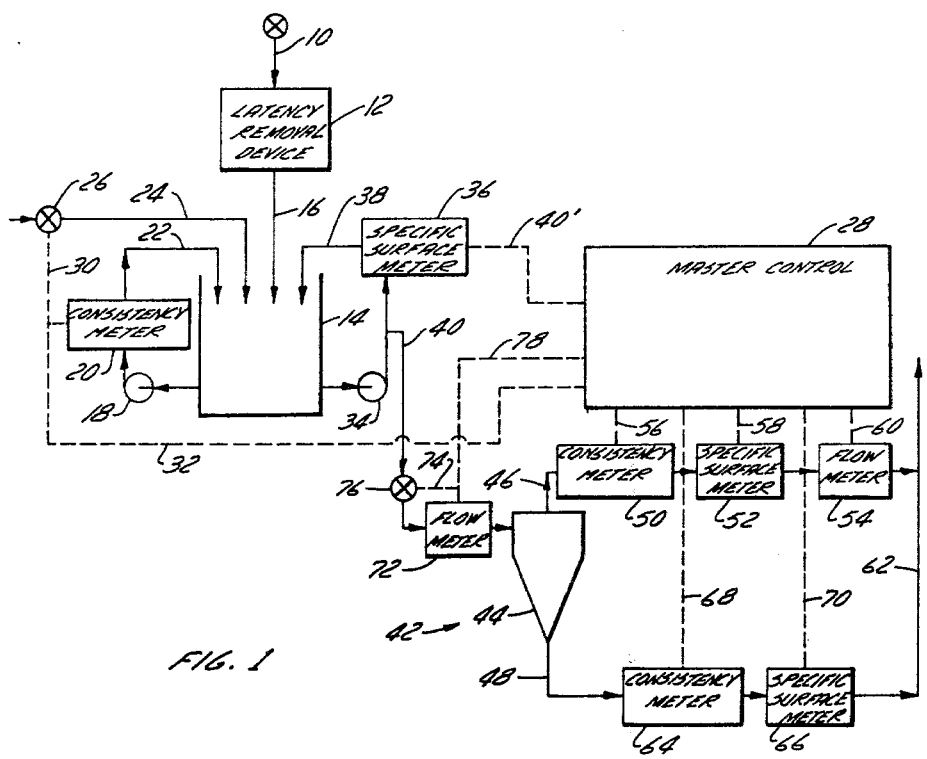
FIG. 1 is a schematic illustration of the monitoring system of the present invention.

As shown in FIG. 1 a pulp sample bled from the mechanical pulping process enters the system by line 10 and depending on the point in the mechanical pulping arrangement from which the sample is taken, it passes through a latency removal device 12 and then enters the container 14 via the line 16.

A suitable principle for liberating the latent properties in mechanical pulp relatively quickly is used in a laboratory disintegrator sold under the name Domtar Disintegrator by Noram Quality Control and Research Equipment Ltd. This device releases the latent properties of a mechanical pulp by rapidly recirculating the pulp through a centrifugal pump (the pulp being at a temperature of about 90°-95° C.).

Pulp from the container 14 is pumped via pump 18 to consistency meter 20 and is returned to the container 14 via line 22.

The requirements of a consistency meter 20 for use in an on-line monitoring system are such that it should measure consistency independent of other fibre properties (i.e. fibre length and specific surface) and should be capable of measuring absolute consistencies with an accuracy and reproducibility within ±5% of the absolute value. Thus in consistency meters for use in the present invention the principle for consistency determination should be a direct one, namely it should be based on the definition consistency. Most consistency meters measure consistency indirectly i.e. they measure other pulp properties, such as, resistance to flow, dielectric properties of the pulp suspension etc., which are related to consistency as well as other fibre properties.

Techniques have been proposed for determining consistency of a pulp free of other characteristics of the pulp by sensing directly the density of the pulp slurry. For example, Thiessen and Dagg proposed sensing the vibrations resulting from an inbalanced rotor to determine the density of a liquid compared with a control liquid using a rotating sample container and determining the imbalance of the system (see Pulp & Paper Magazine of Canada, September 1959).

It is also proposed to use a Sperry Gravitymaster to determine consistency directly independent of other pulp properties. This device uses a gravity balance technique to determine the changing weight of the given size sample. (See Measurement and Control Vol. 1 Nov. 11, 1968 pages T179 to T186)

Neither of the above two devices are believed to currently be available on the market.

If one is to measure consistency directly using either of the above techniques or the one proposed hereinbelow it is essential that the sample be substantially free of or contain known quantities of extraneous matter, in particular there be no air in the sample and any extraneous material with the fibres (fillers etc.) be accurately known before the consistency can be determined. Also it is important that the temperature be accurately controlled or known since a change in temperature will change the accuracy of the instrument although the instrument can be calibrated for different temperatures.

It has now been found that an instrument known as a density cell such as that sold under the tradename "Dynatrol" Cl-10HY manufactured by Automation Products, Houston, Texas can provide a very accurate indication of consistency independent of other pulp properties. This device measures the change in frequency of a vibrating tube through which the pulp suspension is continuously passed and thereby a continuous indication of the consistency of the stock is obtainable for stock consistencies in the range of about 0.1 to 1.5% which is the consistency range in which the present invention operates.

The consistency meter 20 measures a consistency of the stock in the container 14 and preferably adjusts the water (essentially free of fibre and other solids) in-put through line 24 via control valve 26 to maintain the consistency of the stock in the container 14 substantially constant.

The dash lines used in FIG. 1 indicate control lines from the various instrumentalities to the various elements controlled and to the master control 28.

It will be noted that the consistency meter 20 is connected to the valve 26 via control line 30 and to the master control 28 via line 32. In the event that the consistency in the tank 14 is always maintained constant, the control line 32 may be omitted since it will not be variable in the system.

Stock in the tank 14 is also circulated via a pump 34 through a specific surface meter 36 and returned to the tank 14 via line 38. The specific surface meter 36 directs a signal to the master control 28 via the control line 40[1]. This provides the average specific surface of the pulp.

SPECIFIC SURFACE MEASUREMENT

Generally, specific surface meters use the permeability method to determine specific surface, however, such a method is not particularly suited for on-line measurement.

A more suitable means for measuring specific surface has been found utilizing an optical method that senses scattered light from a pulp sample i.e. a device known as a turbidity meter which is normally used to determine solids concentration in a slurry. The light scattered from an assembly of pulp fibres in the pulp sample may be considered to be proportional to the number of particles per unit volume of suspension and their area i.e.

$$T = KNA$$

Where T is the amount of scattered light (meter reading) K = a constant dependent on refractive index of the fibres and their size relative to the wavelength of the light used, N = number of particles, and A = average area of a particle. The consistency of the stock is C = Nm where m is the average mass of a particle, thus $$T = KC(A)/m$$

and the term A/m is the area per unit mass, i.e. the specific surface of the particle, therefore, $$T = KC(SS)_g \text{ or } (SS)_g = T/KC$$

$(SS)_g$ is the average specific surface of the fibre network. The subscript (g) is used to denote a geometric specific surface or light scattering area, in contrast to the hydrodynamic specific surface measured by the permeability method. However, these two specific surfaces, while they are not necessarily the same numerically have a definite correlation between them.

For 130 pulp samples which included, stone groundwood, refiner and thermomechanical pulps, chemical pulps and mixtures of chemical fibres with stone groundwood the experimental results were correlated with the following regression equation.

$$(SS) = 8.92 \times 10^{-7} (JTU)^{1.77} (C_g)^{-2.16} \qquad 2$$

where (SS) is the average (hydrodynamic) specific surface in meters squared per gram, JUT is the turbidity meter reading in Jackson turbidity units and $C_g$ is the consistency in %. $R^2$ - the Coefficient of Determination for equation 2 is 0.88 indicating that 88% of the variations of specific surface is explained by variations in JTU and $C_g$.

Figure 2:
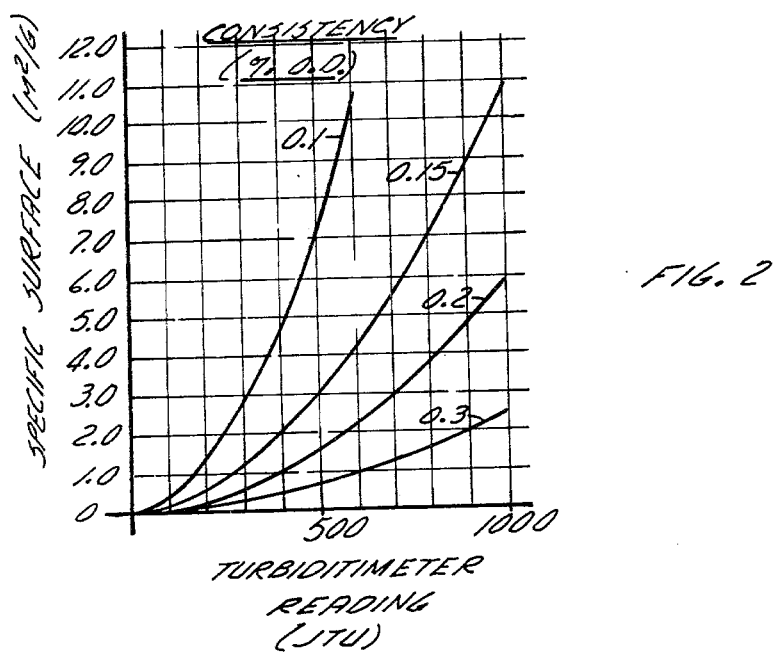
FIG. 2 is a plot of specific surface in meters squared per gram vs the turbidity meter reading in Jackson Turbidity Units (JTU) showing the effect of consistency change on the relationship of specific surface to the turbidity meter reading.
Figure 4:
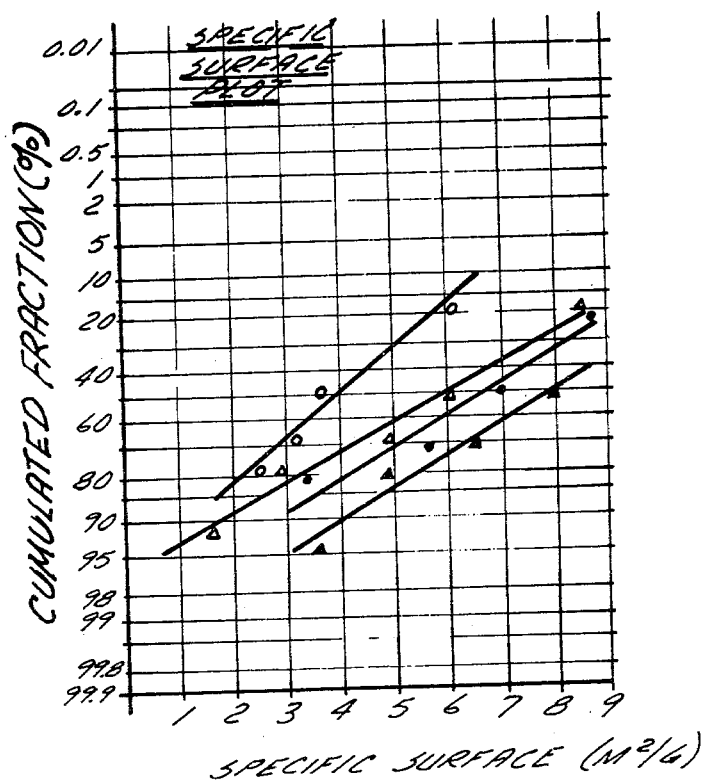
FIG. 4 is plot of cumulative weight fraction as a percent of feed vs specific surface in meters square per gram on normal probability paper.

FIG. 2 is a plot of equation 2 at different consistencies showing the relationship found between specific surface and the turbidity meter reading. It will be apparent that the turbidity meter provides a good easy and quickly operating technique for determining the specific surface of a pulp sample.

The light scattering proportion of the pulp assembly can be measured by a commercially available turbidity meter, the specific model used in the present invention is a DRT-1000 on-line turbidity meter manufactured by HF Instruments, Bolton, Ontario. Turbidity meters generally pass a light beam through a suspension and measure the scattered light on opposite sides of the light beam (at an angle of 90° to the beam) as well as the light projected through the suspension (in line with the light beam).

Figure 3:
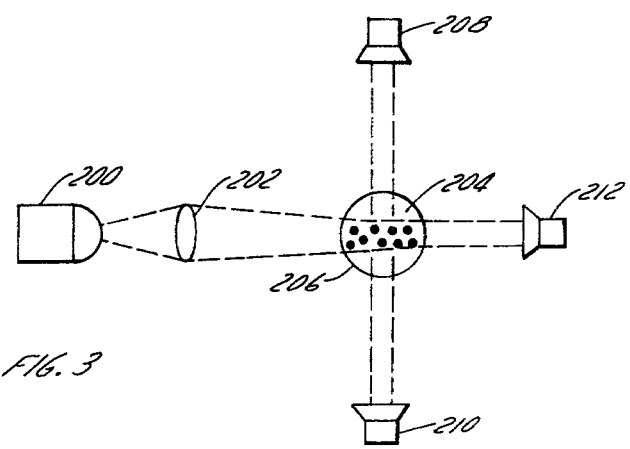
FIG. 3 is a schematic diagram of a turbidity meter.

FIG. 3 has schematically illustrated a Turbidity Meter which is provided with a light source 200, passing light through a lens 202 and through a sample 204 continuously passing through the transparent pipe section or tube 206. Three detectors 208, 210 and 212 are arranged to detect the light reflected from and passing through the sample i.e. the detectors 208 and 210 detect the amount of reflected or scattered light on opposite sides of the sample and the detector 212 detects light transmitted through the sample. The light source 200, pipe 206 and detector 212 are on a straight line and the detectors 208 and 210 and pipe 206 are also positioned on a straight line with the two lines so formed being substantially mutually perpendicular.

The specific surface meters used in the present invention such as meter 36 are in fact turbidity meters which are operated in conjunction with a consistency meter (or a fixed consistency) to determine the specific surface of the pulp fraction or feed pulp based on the curves such as those shown in FIG. 2.

The consistency meter 20 and specific surface meter 36 (turbidimeter), describe the consistency and specific surface of the feed pulp.

SPECIFIC SURFACE DISTRIBUTION

The pulp is pumped by pump 34 through line 40 to the specific surface measuring instrumentalities generally indicated at 42 and which include a hydrocyclone 44 having an overflow (base) outlet line 46 and an underflow (apex) outlet line 48. Consistency meter 50, specific surface meter 52, (turbidity meter), and flow meter 54 measure respectively the consistency, specific surface and rate of flow of fibre through the overflow outlet line 96. The outputs from these meters are fed via lines 56, 58 and 60 respectively to the master controller 28 and the stock in line 46 is returned to the system via line 62.

The consistency and specific surface of the underflow fraction in line 48 may also be measured by the consistency meter 64 and the specific surface meter 66 (turbidity meter). The outputs from these meters are fed via lines 68 and 70 respectively to the master controller 28 and the stock in line 48 is returned to the system via line 62.

Flow to the instrumentalities 42 and particular to the hydrocyclone 44 is controlled via the control flow meter 72 which via line 74 controls the valve 76 and thus the flow through line 40.

The flow meter output may be connected to the master controller 28 via line 78 but obviously if flow to the hydrocyclone 44 is maintained substantially constant there needn't be a direct input from the flow meter 72 to the master control 28.

The consistency in line 48 or 46 can be calculated since the consistency and flow of the stock entering the system is known and the consistency and flow stock in the line 46 or 48 is determined.

The instrumentalities 42 input the master controller 28 with the specific surface and weight fraction of the overflow and underflow fraction and the specific surface of the feed pulp is provided via meter 36.

A laboratory method of determining specific surface distribution employs a hydrocyclone means in which the sample is cascaded and the weight fractions and specific surface of the various underflow and/or overflow fractions are measured, thereby to determine the distribution curve of the fibres specific surface. When such data for a mechanical pulp or chemi mechanical pulp is plotted on cumulative normal probability paper as cumulative specific surface fraction by weight as a percentage of feed vs specific surface it has been found that they approximate a straight line relationship over the significant range of the specific surfaces of the fibres in the pulp. In principle then, only two points are needed to determine the entire fibre specific surface distribution over the range.

Typical cumulative probability curves of specific surface are shown in FIG. 3. These curves were developed from lab data and show the accurate linear relationship of cumulative specific surface fraction as a percent of feed vs specific surface plotted on the cumulative probability paper. The hollow and solid circles designate two different thermo mechanical pulps and the hollow and solid triangles two different groundwood pulps.

In the specific on-line sensor of the present invention, the hydrocyclone 44 had a major diameter of 51 mm and was equipped with a 7.9 mm underflow opening. The flow, consistency and specific surface (turbidity) of the feed, underflow and overflow fractions are measured (or calculated) using the input to the master controller 28 from the consistency meter 20, flow meter 72, consistency meter 50, specific surface meter 52, flow meter 54, consistency meter 64 and specific surface meter 66. Using the straight line relationship the distribution of specific surface over the range can be obtained as well as the low specific surface fraction of the pulp which is important for determining linting.

Alternatively or as a check the specific surface of the feed as measured by meters 36 and 20 and its flow (meter 72) and the specific surface of the overflow measured by meter 62 and 60 and its flow (meter 64) (or the underflow fraction line 48) may be used to obtain the required points on the curve. Any two of the underflow, overflow or feed may be measured to obtain the required two points from a material balance of the hydrocyclone.

It will be apparent that the specific surface distribution and average specific surface of the pulp is obtainable using the (or selected ones of the) instrumentalities 42 and that the pulp sample used to determine these parameters is returned to the system via lines 46 and 48 which connect with line 62.

Modification may be made without departing from the spirit of the invention as defined in the appended claims.

We claim:

1. A method for on line determining the fibre specific surface distribution by weight of a pulp comprising, continuously separating a feed sample of said pulp in a hydrocyclone means into an overflow fraction and an underflow fraction measuring the parameters of at least two of said feed and each of said fractions required to determine their fibre mass flow rates and average specific surfaces, determining the said fibre mass flow rate and average specific surfaces, determining the specific surface distribution by weight of said feed sample based on said mass flow rates and the specific surfaces of said at least two of said feed and said fractions and a substantially cumulative normal distribution relationship for said pulp of cumulative specific surface fraction as a % by weight of feed to specific surface.

2. An apparatus for determining the fibre specific surface distribution by weight of a pulp comprising, hydrocyclone means having an overflow outlet and an underflow outlet, means for feeding said pulp to said hydrocyclone means thereby to fractionate said pulp into an underflow fraction and an overflow fraction, means for measuring the parameters of at least two of said feed, said overflow and said underflow fractions required to determine their fibre mass rates and average specific surfaces, means for determining said fibre mass flow rates and average specific surfaces, computing means for determining the fibre specific surface distribution of said pulp based on said fibre mass flow rates and specific surfaces and a cumulative normal distribution relationship for said pulp of cumulative specific surface fraction as a percent by weight of feed to specific surfaces.

3. An apparatus as defined in claim 2 wherein said means for measuring said parameters each comprises means for measuring the rate of flow and means for measuring the consistency of the pulp being measured, said means for measuring consistency providing a measure of consistency substantially independent of other characteristics of the pulp.

4. An apparatus as defined in claim 2 wherein each of said means for measuring specific surface comprises means for measuring the consistency substantially independent of other characteristics of the pulp and means for measuring the turbidity of the pulp being measured.

5. An apparatus as defined in claim 4 wherein said means for measuring turbidity includes means for measuring scattered light reflected from the pulp being measured.

6. An apparatus as defined in claim 4 wherein said means for measuring specific surface further comprises means for determining said specific surface based on a predetermined relationship of measured turbidity and consistency to specific surface.

7. An apparatus as defined in claim 5 wherein each said means to measure said parameters includes means to measure the rate of flow and means to measure the consistency of the pulp being measured, and said means for measuring consistency measures consistency substantially independent of other characteristics of the pulp.

* * * * *